United States Patent
Vigano' et al.

(10) Patent No.: US 8,877,770 B2
(45) Date of Patent: Nov. 4, 2014

(54) POLYMORPH OF RIFAXIMIN AND PROCESS FOR THE PREPARATION THEREOF

(75) Inventors: Enrico Vigano', Lurago d'Erba (IT); Renato Molteni, Inverigo (IT); Simona Lanfranconi, Montano Lucino (IT); Massimiliano Arrighi, Luisago (IT); Fabio Gatti, Lurate Caccivio (IT)

(73) Assignee: Clarochem Ireland Limited, Dublin (IE)

( * ) Notice: Subject to any disclaimer, the term of this patent is extended or adjusted under 35 U.S.C. 154(b) by 0 days.

(21) Appl. No.: 14/118,740

(22) PCT Filed: May 18, 2012

(86) PCT No.: PCT/IB2012/052506
§ 371 (c)(1),
(2), (4) Date: Nov. 19, 2013

(87) PCT Pub. No.: WO2012/156951
PCT Pub. Date: Nov. 22, 2012

(65) Prior Publication Data
US 2014/0107144 A1     Apr. 17, 2014

(30) Foreign Application Priority Data
May 19, 2011  (IT) .............................. MI2011A0890

(51) Int. Cl.
*A61K 31/437*     (2006.01)
*C07D 498/22*     (2006.01)

(52) U.S. Cl.
USPC .......................................... 514/279; 540/457

(58) Field of Classification Search
USPC .................................... 514/279; 540/457, 456
See application file for complete search history.

(56) References Cited

U.S. PATENT DOCUMENTS

2005/0101598 A1   5/2005   Viscomi et al.
2010/0174064 A1   7/2010   Gushurst et al.

FOREIGN PATENT DOCUMENTS

EP   1698630     9/2006
WO   2009108730   9/2009

OTHER PUBLICATIONS

International Search Report issued in counterpart PCT Application No. PCT/IB2012/052506 on Jul. 24, 2012.
Written Opinion of International Searching Authority issued in counterpart PCT Application No. PCT/IB2012/052506 on Jul. 24, 2012.
International Preliminary Report on Patentability issued in counterpart PCT Application No. PCT/IB2012/052506 on Jul. 4, 2013.

*Primary Examiner* — Charanjit Aulakh
(74) *Attorney, Agent, or Firm* — Silvia Salvadori, P.C.

(57) ABSTRACT

The present invention relates to a new polymorph of Rifaximin, designated κ, and to a process for the preparation thereof. Under certain aspects, the invention also relates to pharmaceutical compositions comprising an effective amount of the polymorphic form κ of Rifaximin and a pharmaceutically acceptable carrier and its uses in the treatment of gastrointestinal conditions.

18 Claims, 10 Drawing Sheets

POLYMORPH OF RIFAXIMIN AND PROCESS FOR THE PREPARATION THEREOF

This application is a U.S. national stage of PCT/IB2012/052506 filed on May 18, 2012, which claims priority to and the benefit of Italian Application No. MI2011A000890 filed on May 19, 2011, the contents of which are incorporated herein by reference in their entirety.

FIELD OF THE INVENTION

The present invention relates to a polymorph of Rifaximin and to a process for the preparation thereof, as well as to pharmaceutical compositions which comprise it.

PRIOR ART

Rifaximin, IUPAC name: (2S,16Z,18E,20S,21S,22R,23R,24R,25S,26S,27S,28E)-5,6,21,23,25-pentahydroxy-27-methoxy-2,4,11,16,20,22,24,26-octamethyl-2,7-(epoxypentadeca-[1,11,13]-trienimmino)-benzofuro-[4,5-e]-pirido-[1,2-α]-benzimidazol-1,15(2H)-dione,25-acetate, is the compound of formula (I):

Rifaximin is broad-spectrum antibiotic belonging to the family of rifamycins, devoid of systemic activity. In view of its physicochemical properties, it is not adsorbed in the gastrointestinal tract and therefore exerts its antimicrobial action inside the gastrointestinal tract. Rifaximin therefore has applications in the treatment of diarrhoea and of microbial infections of the gastrointestinal tract typically caused by $E.$ $coli$, a microorganism which, being incapable of passing through the mucosa of the gastrointestinal tract, remains in contact with the gastrointestinal fluids. Rifaximin also has applications for the treatment of irritable bowel syndrome, Crohn's disease, diverticulitis and for antibiotic prophylaxis preceding surgical operations on the intestines.

Rifaximin was described for the first time in the U.S. Pat. No. 4,341,785 together with a process for its preparation, and a method for the crystallisation thereof. However, this patent does not mention the polymorphism of Rifaximin.

As it is generally known, polymorphism derives from the possibility, for the molecule, of modifying its conformation, giving rise to different intermolecular and intramolecular interaction schemes, in particular, hydrogen bonds, which stabilise different spatial arrangements of the atoms.

The possibility for an organic compound of having polymorphism is never foreseeable, so as it is not possible to predict the number of polymorphs of a substance, their stability (which determines the time for which the active principle or a pharmaceutical composition containing it may be stored), their solubility in different solvents (which may have repercussions on the working processes necessary for formulating the compound in a drug composition), their bioavailability, and other characteristics relevant to the pharmaceutical applications.

Polymorphic forms of Rifaximin, and processes for their synthesis and purification, are described in various documents of the known art.

Patent application EP 1557421 A1 describes three polymorphs of Rifaximin. The first form, designated α, has a powder X-ray diffraction (XRD) spectrum which presents peaks at the values of angle 2θ of 6.6°, 7.4°, 7.9°, 8.8°, 10.5°, 11.1°, 11.8°, 12.9°, 17.6°, 18.5°, 19.7°, 21.0°, 21.4° and 22.1°. The second form, designated β, has a powder X-ray diffraction (XRD) spectrum with peaks at the values of angle 2θ of 5.4°, 6.4°, 7.0°, 7.8°, 9.0°, 10.4°, 13.1°, 14.4°, 17.1°, 17.9°, 18.3° and 20.9°. Finally, the third polymorphic form cited in this application, designated γ, has a lesser degree of crystallinity and has a powder X-ray diffraction (XRD) spectrum with peaks at the values of angle 2θ of 5.0°, 7.1° and 8.4°.

Patent application WO 2006/094662 A1 describes two polymorphic forms of Rifaximin, designated δ and ε, respectively; the first has a water content within the range from 2.5 to 6% by weight (preferably from 3 to 4.5%), and a powder XRD spectrum which has peaks at the values of angle 2θ of 5.7°, 6.7°, 7.1°, 8.0°, 8.7°, 10.4°, 10.8°, 11.3°, 12.1°, 17.0°, 17.3°, 17.5°, 18.5°, 18.8°, 19.1°, 21.0° and 21.5°; the second has a powder XRD spectrum with peaks at the values of angle 2θ of 7.0°, 7.3°, 8.2°, 8.7°, 10.3°, 11.1°, 11.7°, 12.4°, 14.5°, 16.3°, 17.2°, 18.0° and 19.4°.

Finally, patent application WO 2009/108730 A2 describes further forms of Rifaximin. In particular, this document describes a ζ form, a η form and a ι form. In this document, the ζ form is identified by 9 different possible groups of characteristic peaks, the η form by 16 different possible groups of characteristic peaks, and the ι form by 20 different possible groups of characteristic peaks, that are not reported here.

Since the crystalline form and the morphology of a solid form of a pharmaceutical compound can influence its physicochemical and biological properties, even to a considerable extent, the research for new polymorphic forms of known pharmaceutical compounds is directed towards finding new polymorphs of Rifaximin, with improved pharmacological properties (a lower required dosage, more rapid action, etc).

One of the objects of the present invention is to provide a new polymorphic form of Rifaximin, and to provide a process for the production thereof.

SUMMARY OF THE INVENTION

The inventors of the present patent application have now identified a new crystalline or polymorphic form of Rifaximin.

In accordance with a first aspect, the present invention relates to a new polymorph of Rifaximin, designated κ, which has a powder XRD spectrum with peaks at the values of angle 2θ of 5.3°, 6.8°, 7.8°, 8.5°, 9.3°, 10.1°, 10.3°, 12.1°, 12.7°, 13.4°, 13.7°, 14.6°, 15.3°, 15.8°, 16.4°, 16.9°, 17.7°, 18.0°, 18.8°, 19.2°, 19.7°, 20.3° and 22.1°.

The inventors of the present patent application have found that the polymorph κ of the invention tends to keep its crystalline form even in the presence of moisture. This characteristic of the polymorph κ of the invention makes it more stable than other already known crystalline forms of Rifaximin and enables the storage, even for prolonged time periods, of pharmaceutical formulations incorporating it as an active pharmaceutical ingredient.

Under a second aspect, the invention provides a process for preparing the new polymorph cited above.

Advantageously from the industrial point of view, the invention provides for a variable and flexible process for the production of the polymorph κ.

In accordance with a third aspect, the present invention provides for pharmaceutical compositions comprising a therapeutically effective amount of the polymorph of Rifaximin designated κ or derivatives thereof, and a pharmaceutically acceptable carrier.

According to one embodiment, the polymorph κ of Rifaximin is provided for use as a medicament.

In accordance with a fourth aspect, the present invention provides therapeutic uses and therapeutic treatment methods which use the pharmaceutical compositions comprising the polymorph of Rifaximin designated κ.

DETAILED DESCRIPTION OF THE INVENTION

Figure 1:
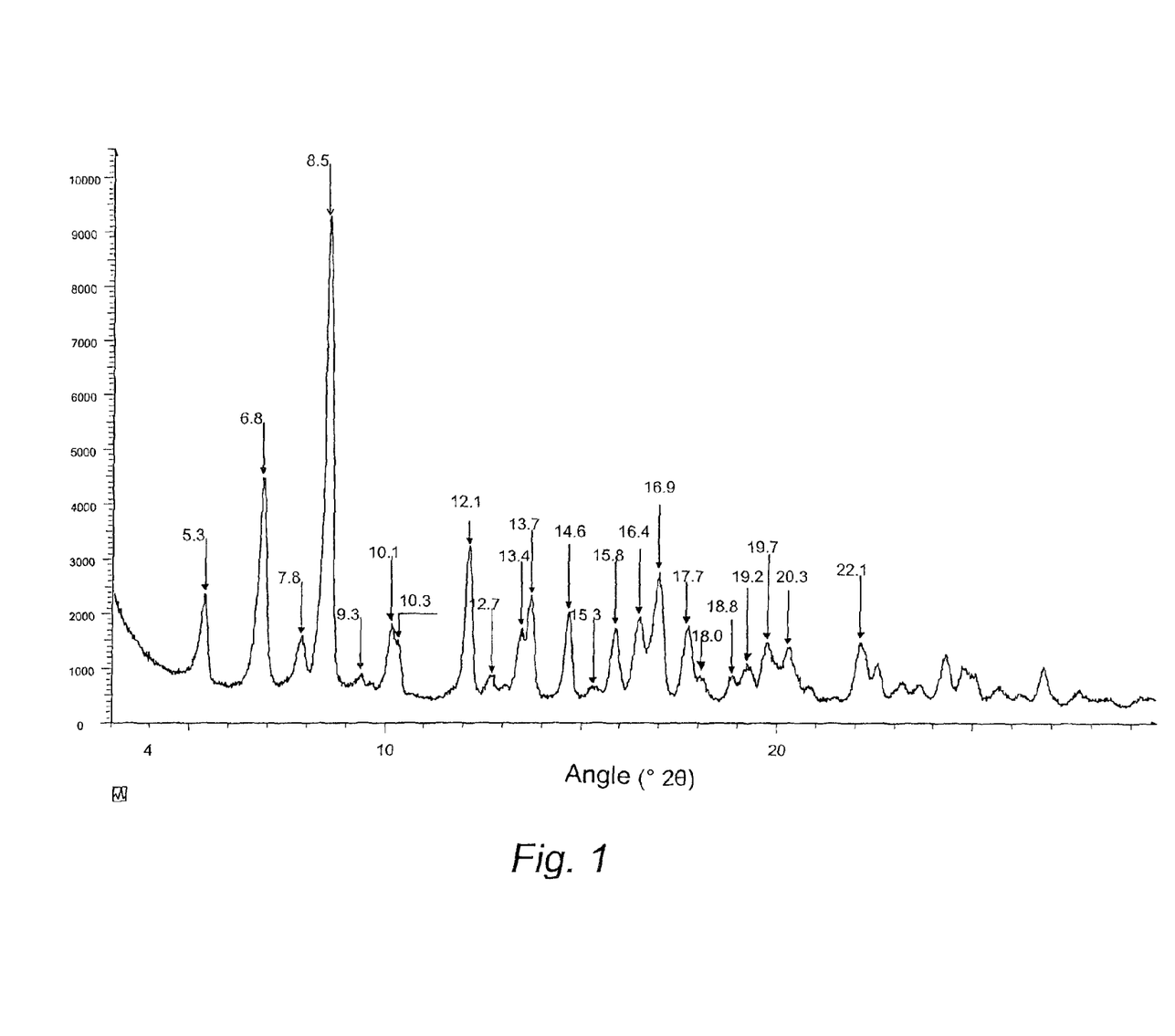
FIG. 1 shows the X-Ray powder diffractogram indicating the position of the peaks which characterise the polymorph κ of the present invention.

According to a first aspect, the invention relates to a new polymorph of Rifaximin, form κ, which, as shown in FIG. 1, in a powder X-ray diffraction analysis shows peaks at values of angle 2θ of 5.3°, 6.8°, 7.8°, 8.5°, 9.3°, 10.1°, 10.3°, 12.1°, 12.7°, 13.4°, 13.7°, 14.6°, 15.3°, 15.8°, 16.4°, 16.9°, 17.7°, 18.0°, 18.8°, 19.2°, 19.7°, 20.3° and 22.1°.

This group of peaks is not similar to any of the characteristic groups of the various polymorphs known in the literature; even though a number of peaks appear in positions corresponding (within the limits of experimental error) to a number of typical peaks of the other forms cited, some of the peaks of the diffractogram in FIG. 1 do not show correspondence to the characteristic peaks of the other forms; even more importantly, the diffractogram of FIG. 1 does not exhibit all the peaks of any one of the known forms α to η, being this a condition to say that it is present (for example in mixture) in the product obtained with the process of the invention. Consequently, the diffractogram of FIG. 1 cannot be associated with any other previously known form of Rifaximin.

As used within the scope of the present invention, the term "polymorph" refers to a property of a compound to cristallize in one or more crystalline forms.

The polymorphs are therefore distinct solids which share the same molecular formula, but each polymorph can have distinct physical properties. Consequently, a single compound can give a variety of polymorphic form and each form can possess different and distinct physical properties, such as solubility profiles, melting-point temperatures, density, hygroscopicity, particle size, fluidity and/or X-ray diffraction peaks.

It is possible to distinguish the different crystalline forms using direct laboratory techniques such as crystallographic methods, in particular with X-ray diffraction or with infra-red spectroscopy or by means of indirect techniques by verifying the differences in the chemical and/or physical properties associated with each specific polymorph.

The polymorph κ has been characterised as it will be evident from the experimental section, and resulted to correspond to a crystalline form having an orthorhombic crystalline cell and belonging to the spatial group $P222_1$.

Specifically, the following cell values were identified:

| | |
|---|---|
| a (Å) | 24.07 ± 7 |
| b (Å) | 22.98 ± 5 |
| c (Å) | 15.34 ± 5 |
| α (deg) | 90.00 |
| β (deg) | 90.00 |
| γ (deg) | 90.00 |

The inventors have surprisingly found that, even at elevated values of relative humidity (RH), conditioning of the Rifaximin polymorph κ of the invention does not produce any significant structural variation of the crystalline form.

For example, by exposing a sample of the polymorph κ to 80% relative humidity for a period of 24 hours, the mass of the sample is found to increase of about 3%, attributable to surface adsorption of water, without registering significant changes in the XRPD pattern.

Surprisingly and advantageously, the polymorph κ of the present invention resulted to be stable when subjected to an 80% humidity level, even for prolonged time periods, as it will be evident from the experimental section which follows. The increase of mass becomes stable after only 4 days at a value of approximately 4.5%, which value does not vary even after 5 months, if the sample continues to be kept under the same humidity conditions.

The polymorph κ of the invention thus has the advantage of not converting into other crystalline forms of Rifaximin and of keeping stable even when placed in a humid environment or in contact with water vapour present in the air and for long periods even in the presence of high humidity levels.

In a second aspect, the invention relates to the process for obtaining the polymorph κ of Rifaximin described above.

In certain embodiments, the process of the invention comprises the stages of placing Rifaximin in contact with a 1,2-dimethoxyethane based solvent, recovering the product and drying to remove said 1,2-dimethoxyethane based solvent.

In one embodiment, the invention comprises the following steps:

suspending or dissolving Rifaximin in 1,2-dimethoxyethane or in a solvent mixture comprising 1,2-dimethoxyethane, in ratios by weight such that the molar ratio of 1,2-dimethoxyethane:Rifaximin is 1:1 or higher;

filtering the obtained precipitate;

drying the filtered product at a temperature of at least 60° C.

The process of the invention resulted to be highly advantageous because it guarantees the κ form to be obtained in high yields while still providing a high degree of variability of the various steps.

In certain embodiments, the invention provides for adding the Rifaximin in the first step to 1,2-dimethoxyethane or to a mixture thereof with other solvents or for adding 1,2-dimethoxyethane or a mixture thereof with other solvents to non-dried Rifaximin.

Advantageously, the first step of the process of the invention can take place within a broad temperature range, preferably at room temperature, but also at temperatures higher or lower than room temperature, compatibly with the boiling point of the solvent, whether this is 1,2-dimethoxyethane or mixtures thereof.

In certain embodiments the filtration step is advantageously carried out at room temperature.

In certain embodiments, the starting Rifaximin may be amorphous or in the form of any of its previously known polymorphs; the initial product may be acquired, or prepared just before the process of the invention, for example according to the procedure described in EP 1557421 A1. In further embodiments of the invention, the polymorph κ can be obtained starting from mixtures of known polymorphs and/or with percentages of amorphous Rifaximin.

According to one embodiment, the process is carried out in a protected atmosphere, for example under nitrogen flow.

In one embodiment, the Rifaximin is either suspended or dissolved in 1,2-dimethoxyethane.

According to one embodiment, when 1,2-dimethoxyethane is used as the unique solvent of Rifaximin, the minimum amount of the solvent used for the purposes of the invention is 3 ml per gram of Rifaximin. Contrarily, there is no upper limit on the amount of solvent per gram of Rifaximin, beyond which the process of the invention can not be reproducible; the amount of solvent is therefore limited by practical considerations, and in particular by the necessity to limit the solvent volumes treated to achieve an economically efficient process (large amounts of solvent involve, for example, long filtration times, large amounts of energy for heating said solvent, etc). In one embodiment, the inventors have observed that a practical upper limit on the amount of solvent may be set at 10 ml per gram of Rifaximin.

Typically, for solvent volume/Rifaximin gram ratios close to the lower limit cited above, one never achieves complete dissolution of the compound, which therefore remains in suspension and undergoes a conversion into the κ form solid-state. Conversely, with higher dilutions initial dissolution may be observed, which is then followed by precipitate formation.

In certain embodiments, Rifaximin is suspended or dissolved in a mixture of solvent comprising 1,2-dimethoxyethane.

According to one embodiment, when the solvent of Rifaximin is a mixture of solvent comprising 1,2-dimethoxyethane, the latter component is used in amounts of at least 0.12 g per gram of Rifaximin. Solvents that are useful for the present invention in combination with 1,2-dimethoxyethane are, for example, n-heptane, methanol, acetonitrile, R—COO—$R^1$ esters wherein R and $R^1$ are independently $C_3$-$C_6$ alkyl radicals, and $C_3$-$C_7$ alkyl ketones, ethanol, isopropanol and water; the solvent mixture may also comprise more than one of these further solvents.

In certain embodiments, once the precipitate has been obtained, it may be filtered, by washing with a suitable solvent, for example, 1,2-dimethoxyethane or n-heptane.

In certain embodiments, the wet product is then dried, for example by treating in a static oven at 60° C. and/or under vacuum.

According to a third aspect of the present invention, pharmaceutical compositions are provided, which comprise a therapeutically effective amount of the polymorph of Rifaximin designated κ or derivatives thereof, and a pharmaceutically acceptable carrier.

The term "pharmaceutically acceptable carrier" comprises one or more pharmaceutically acceptable materials such as, for example, fillers, excipients, diluents, solvents, encapsulating materials involved in the transport or support of a pharmaceutically active substance. The carrier is defined as a pharmaceutically acceptable in the sense of being compatible with the other substances or ingredients of the pharmaceutical composition and of being physiologically acceptable or compatible with the human organism.

In certain embodiments, the composition of the invention comprises one or more excipients, for example, diluting agents, binders, disaggregants, lubricants, buffering agents, humidifiers, dyes, flavourings and/or sweeteners.

By way of example, suitable diluents include mannitol, lactose, sorbitol, suitable binders include gelatins, starches, cellulose derivatives, sugars, natural gums and polyvinyl pyrrolidone, suitable lubricating agents include stearates, talcum, hydrogenated vegetable oils, PEG, suitable disaggregating agents include cellulose, alginates, starches, reticulated polymers.

Suitable pharmaceutical compositions comprising a polymorphic form of Rifaximin according to the invention include oral, topical, rectal, vaginal, parenteral and nasal administration, and those administrated by aerosol.

Pharmaceutical compositions for oral administration may be in solid form, for example in the form of tablets, capsules, cachets, pills, granules or powders, or in liquid form, such as solutions, suspensions, syrups, gels, emulsions, each comprising an effective amount of a polymorphic κ form of Rifaximin.

The amount of the polymorphic κ form of Rifaximin present in the pharmaceutical composition of the invention producing a single dosage form varies as a function of the method of administration and will be equal to an amount which achieves the desired therapeutic or prophylactic effect. In general, this amount can vary from 0.1 to 99% by weight. In some embodiments, said active principle is in the range from 1 to 50% by weight, preferably from 5 to 20% by weight.

The pharmaceutical compositions according to the invention may be prepared according to the standard methods of pharmaceutical technology which provide for mixing the polymorph κ of Rifaximin with a carrier and one or more excipients or further active ingredients. In general, the pharmaceutical composition is prepared by uniformly mixing the polymorph κ of Rifaximin with a suitable carrier in liquid form or a suitable solid carrier finely ground, or with both and thus forming the product where necessary.

The dosage level of the polymorph κ of Rifaximin typically incorporated in the pharmaceutical composition of the invention will vary as a function of the severity of the disease and other conditions, and in accordance with the age of the individual requiring treatment.

The dose of active principle to be administered will typically vary from 20 to 2500 mg per day, preferably from 50 to 1000 mg/day, and more preferably from 100 to 600 mg/day.

According to a fourth aspect of the invention, methods are provided for preventing or treating diseases or intestinal conditions comprising the administration of an effective amount of the polymorph κ of Rifaximin to an individual in need of treatment.

Intestinal diseases or conditions which may be treated include diarrhoea, in particular in the forms associated with microbial infections, for example, from *E. coli* and/or *Clostridium*, traveller's diarrhoea, Crohn's disease, irritable bowel syndrome, enteritis, enterocolitis, diverticulitis, excessive bacterial flora of the small intestine, colitis, pancreatic insufficiency, chronic pancreatitis and/or hepatic encephalopathy.

In certain embodiments, for the therapeutic treatment or prevention of the above-mentioned diseases, the polymorph of the invention may be administered in a concentration from approximately 0.1 to approximately 100 mg per kilo of body weight, preferably from 0.5 to 30 mg/kg, more preferably from 2 to 10 mg/kg of body weight.

The present invention will now be described with reference to the following examples, which are provided for purely illustrative purposes, and must not be understood in a sense limiting the invention.

EXAMPLE 1

10 g of Rifaximin and 50 ml of 1,2-dimethoxyethane were charged into a 200-ml flask under nitrogen flow. This was then left under agitation for approximately half an hour, and after initial dissolution, the formation of a precipitate was noticed in the flask.

The solid was filtered under vacuum and was washed with 10 ml of 1,2-dimethoxyethane. 13.3 g of wet product were obtained, which were dried in an air oven at 30° C. for one night. The following day a weight of 10.4 g was recorded, more than the theoretical weight of 10 g.

A TGA analysis was carried out on the product (with a PerkinElmer Pyris 1 TGA instrument interfaced with a SpectrumOne FT-IR; temperature gradient 10° C./min); the results of the analysis showed a weight loss of 10.93% over the temperature range from 25 to 185° C. Via the FT-IR interface, the spectra of the gases emitted by the sample were continuously acquired during heating in TGA, and it was revealed that the weight loss could be ascribable for the most part to emission of the solvent 1,2-dimethoxyethane.

The sample was left in a static oven at 60° C. for another night. A thermogravimetric analysis was carried out on the sample thus obtained with a 1.76% weight loss, without recording further emissions of 1,2-dimethoxyethane. A control check of the water content were carried out on the same sample according to Karl Fischer method, obtaining a value of 1.4% by weight.

Figure 3:
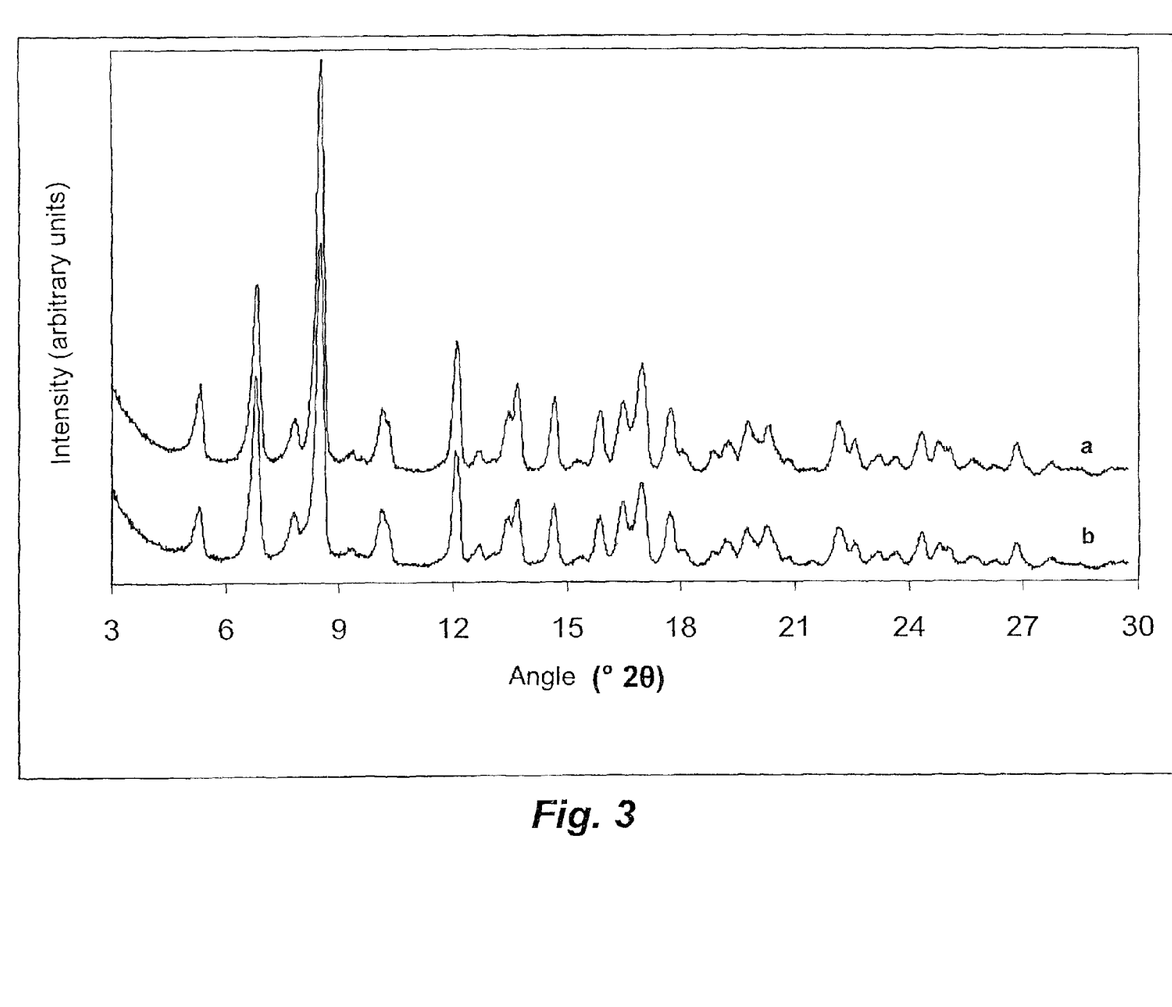
FIGS. 3, 4 and 5 show the powder diffractogram of various samples of polymorph κ according to different methods of preparation.

A powder XRD test was carried out on the product thus obtained. The test was performed using a Bruker D5005 powder diffractometer equipped with a θ-θ vertical goniometer and a Position Sensitive Detector (PSD, Braun). The spectrum was collected in air at room temperature, within the angular interval 2θ within the range from 3 to 30° in a 0.02° stepped modality with a calculation time of 1.25 seconds. This test resulted in the diffractogram shown in FIG. 1, which shows the angular position of the principal peaks characterising the polymorph of the invention; the same diffractogram is also shown in FIG. 3, as pattern a, so as to be able to verify the correspondence of the peaks with those of the sample prepared in the next example.

EXAMPLE 2

7.5 kg of Rifaximin and 50 l of 1,2-dimethoxyethane were charged into a reactor, stirring was started, dissolution occurred, and after 15 minutes spontaneous precipitation was observed. The suspension was left under stirring for 4 h, then centrifuged, and the panel was washed with 15 l of 1,2-dimethoxyethane. 11 kg were isolated, which were dried at 10 mmHg and 80° C.

7.0 kg of a red-orange powder were obtained.

K.F.:1.85; residual content of 1,2-dimethoxyethane of a few ppm, lower than the ICH limit of 100 ppm.

Purity HPLC 99.71%, in conformity with the limits of the present European Pharmacopoeia (seventh edition).

Particle size: d (0.5) 3.20 micron and d(0.9) 6.65 micron.

The Rifaximin sample thus obtained was analyzed and the powder X-ray diffractogram was obtained with the Bruker D5005 diffractometer, radiation CuKα ($\lambda_{K\alpha1}$=1.54056 Å, $\lambda_{K\alpha2}$=1.54439 Å), Nickel filter, on a flat sample carrier made of Si, with a low, diffuse base. The collection was performed within the angular interval 3-50° step 0.015°, time/step 5 sec.

Figure 2:
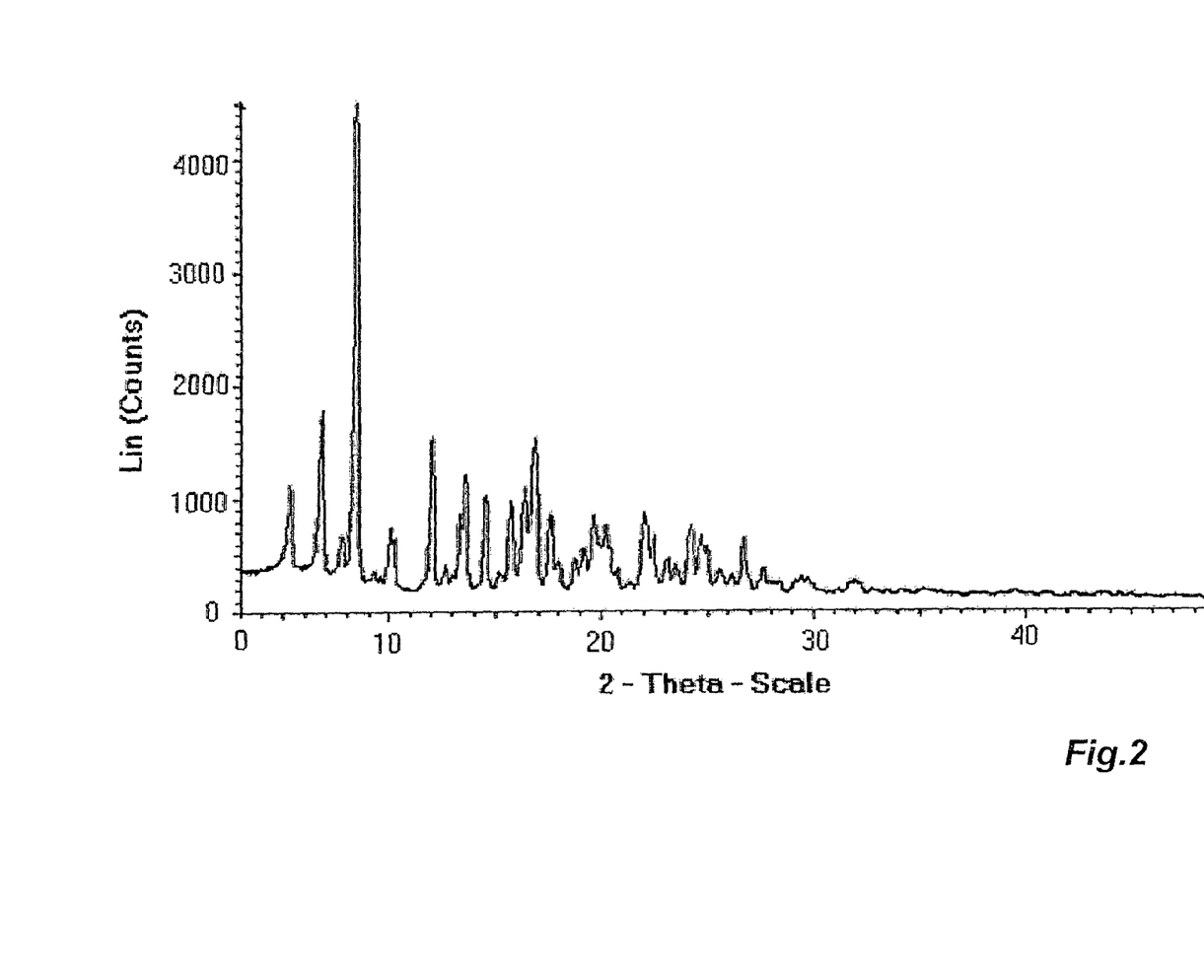
FIG. 2 shows the powder diffractogram with Bruker D5005 diffractogram, radiation CuKα ($\lambda_{K\alpha 1}$=1.54056 Å, $\lambda_{K\alpha 2}$=1.54439 Å), Nickel filter, Position Sensitive Detector, on a flat sample carrier made of Si, with a low, diffuse base of the polymorph κ of the present invention.

The diffractogram obtained is shown in FIG. 2, the pattern corresponding to that in FIG. 1, which relates to the sample obtained an example 1.

X-ray measurements with synchrotron light on the polymorph obtained were carried out on the ID31 line of the synchrotron in Grenoble (France).

The data were collected with monochromatic radiation (λ=1.29994(3) Å) in a boron silicate capillary (1-mm diameter) aligned with the axis of the diffractometer; the data collection was performed within the angular interval 2-40°, step 0.003°. The synchrotron light enabled accurate measurements in which the effects of overlapping of the peaks are reduced and determination of the position of the diffraction peaks is possible with an uncertainty of about 0.01°.

Within the limits of the principal diffraction effects, in Table 1 the values of the interplanar distances d, the angular positions of the peaks, the position recalculated according to Bragg's law for the wavelength CuKα$_1$ (for the purpose of comparing these positions with those obtained from conventional X-ray diffractograms) and the percentage intensities of the diffraction peaks are reported.

TABLE 1

| | λ | | |
|---|---|---|---|
| | 1.29994 | 1.54056 | |
| d | 2θ | | % |
| 16.6365 | 4.478 | 5.308 | 19 |
| 12.9481 | 5.755 | 6.821 | 100 |
| 11.2776 | 6.608 | 7.833 | 15 |
| 10.3745 | 7.184 | 8.517 | 62 |
| 9.4735 | 7.868 | 9.328 | 4 |
| 8.7577 | 8.512 | 10.093 | 12 |
| 8.5949 | 8.674 | 10.284 | 10 |
| 7.3099 | 10.203 | 12.098 | 27 |
| 6.9659 | 10.708 | 12.698 | 7 |
| 6.5935 | 11.315 | 13.419 | 7 |
| 6.4669 | 11.537 | 13.683 | 12 |
| 6.0477 | 12.340 | 14.636 | 12 |
| 5.8229 | 12.818 | 15.204 | 2 |
| 5.6018 | 13.326 | 15.808 | 4 |
| 5.3826 | 13.871 | 16.456 | 8 |
| 5.2124 | 14.327 | 16.998 | 12 |
| 4.9946 | 14.955 | 17.745 | 12 |
| 4.9116 | 15.209 | 18.047 | 2 |
| 4.7130 | 15.854 | 18.814 | 3 |
| 4.6106 | 16.208 | 19.236 | 3 |
| 4.5052 | 16.59 | 19.691 | 4 |
| 4.3786 | 17.074 | 20.266 | 8 |
| 4.0282 | 18.571 | 22.050 | 6 |

A procedure of indicization, which enables cell parameters and parameters for crystalline system of the polymorph κ to be obtained, was applied successfully starting from the position of the diffraction peaks of the collection with synchrotron light. The solution, obtained using Topas4.0 indexing software and tested with CheckCell version Nov. 1, 2004, yielded an orthorhombic cell with spatial group P222$_1$. A procedure of Full Profile Fitting of the diffraction profile by synchrotron light showed that there is an excellent agreement between the experimental diffractogram and the one generated by the orthorhombic cell. The refined cell parameters and the volume of the orthorhombic cell are reported below

| | |
|---|---|
| a (Å) | 24.0773 ± 12 |
| b (Å) | 22.9863 ± 12 |
| c (Å) | 15.3462 ± 10 |
| α (deg) | 90.00 |
| β (deg) | 90.00 |
| γ (deg) | 90.00 |
| Volume (Å$_3$/cell) | 8493.30 ± 15 |

An high agreement was also obtained between the positions of picks generated by the orthorhombic cell and those observed, indicating thus a satisfactory result of the procedure of indicization and confirming that the sample is composed of a single, highly pure crystalline phase.

EXAMPLE 3

2 g of Rifaximin and 6 ml of 1,2-dimethoxyethane were charged into an Erlenmeyer flask and the mass was allowed to agitate until complete dissolution of the starting compound was achieved. Thereafter, a precipitate which remained in suspension was observed to form.

Working at room temperature, 10 ml of n-heptane were added dropwise to the solution obtained, and filtration was performed under vacuum, washing with heptane. The wet product isolated was dried in a static oven at 60° C., obtaining 1.95 g of dry product. On the product thus obtained, a test was performed for the content of residual water, which resulted to be 1.3% by weight, and a thermogravimetric analysis was carried out, which yielded a weight loss of 1.9%.

On the product obtained, a powder XRD test was performed under the same conditions as example 1, which resulted in the diffractogram shown as pattern b in FIG. 3.

EXAMPLE 4

50 g of purified Rifaximin and 500 ml of 1,2-dimethoxyethane were charged into a 1-liter flask under nitrogen flow, and stirring was maintained while checking for total dissolution of the Rifaximin. After approximately 20 minutes, the start of spontaneous crystallisation of an orange solid was observed, which became rapid after further 5 minutes. The suspension was thus left to stir for 2 hours. The solid was then filtered and washed twice with 50 ml of 1,2-dimethoxyethane.

72.1 g of a pale orange wet product were obtained; this product was dried in an oven under vacuum at 80° C. for 24 h, yielding 46.82 g of pale orange dry product.

Figure 4:
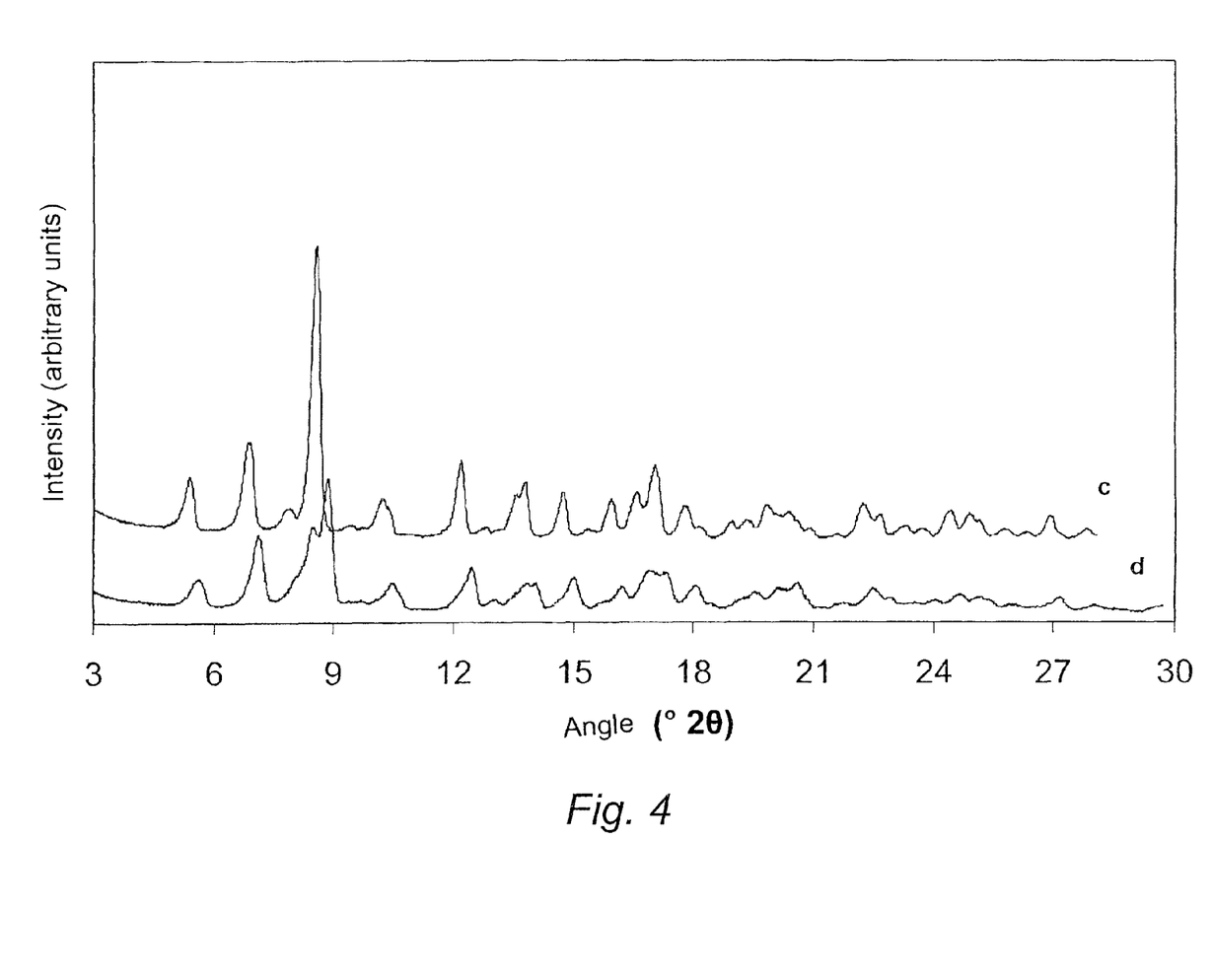

A powder XRD test was performed on the product thus obtained under the same conditions as in example 1, which resulted in the diffractogram shown as pattern c in FIG. 4.

EXAMPLE 5

10 g of purified Rifaximin and 200 ml of 1,2-dimethoxyethane were charged into a 500-ml flask under nitrogen flow, and stirring was maintained until total dissolution of the Rifaximin. After about 10 minutes, spontaneous crystallisation of an orange solid was observed, which immediately became rapid. The suspension was then left to agitate for at least 2 hours. The solid was filtered and washed twice with 10 ml of 1,2-dimethoxyethane.

12.0 g of pale orange product were obtained; this product was dried in an oven under vacuum at 80° C. for 24 h, yielding 8.92 g of pale orange dry product.

A powder XRD test was performed on the product thus obtained under the same conditions as in example 1, which resulted in the diffractogram shown as pattern d in FIG. 4.

EXAMPLE 6

10 g of purified Rifaximin, 10 ml of acetonitrile and 30 ml of 1,2-dimethoxyethane were charged into a 100-ml flask under nitrogen flow, and agitation was maintained while checking for total dissolution of the Rifaximin. After a few minutes, there was massive spontaneous crystallisation of an orange solid which was diluted with 50 ml of n-heptane. The suspension was maintained under agitation at room temperature for 2 hours. The solid was filtered and washed twice with 10 ml of n-heptane.

11.0 g of pale orange wet product were obtained, which was dried in an oven under vacuum at 80° C. for 24 h, yielding 9.52 g of yellow-orange dry product.

Figure 5:
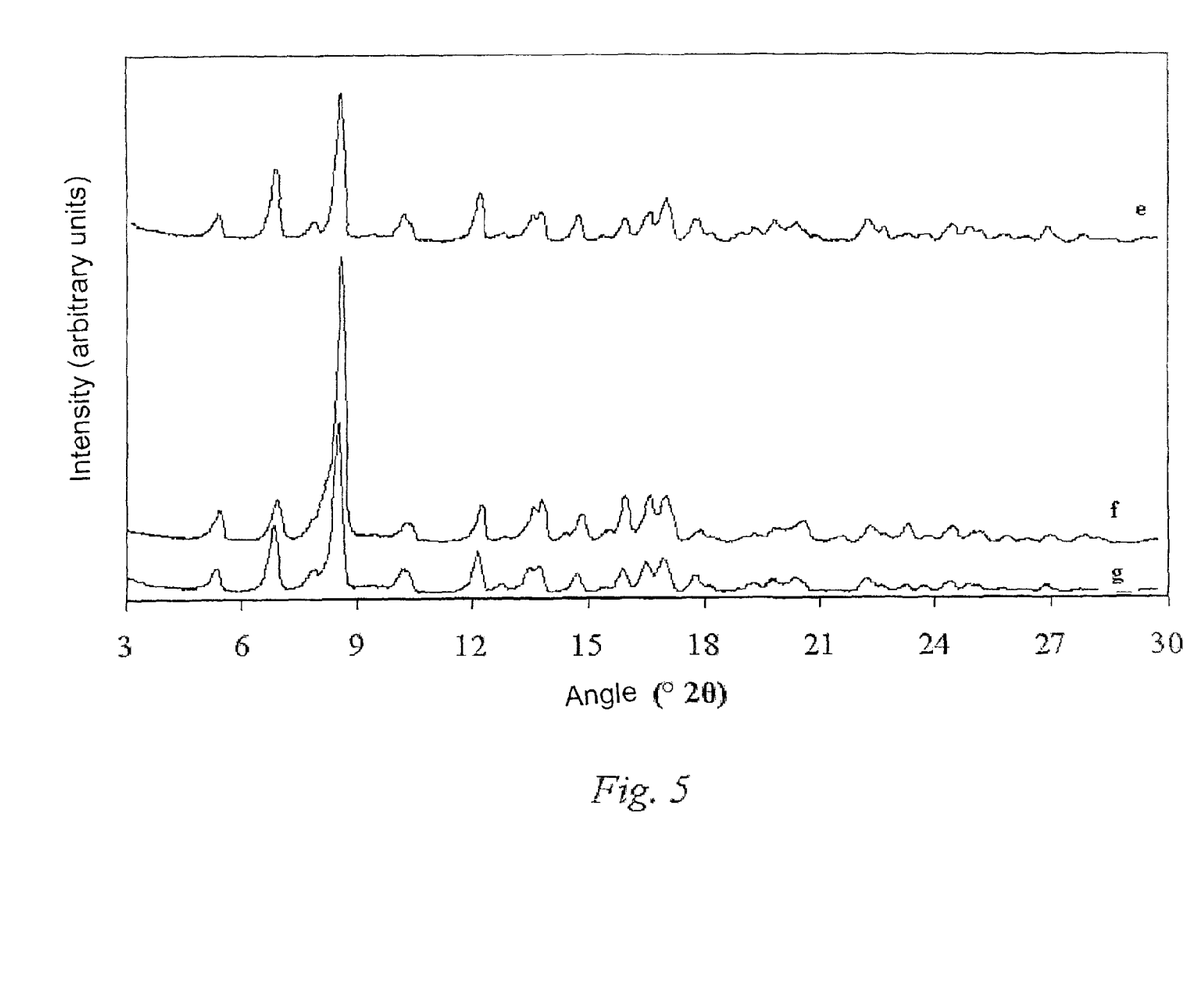
Figure 6:
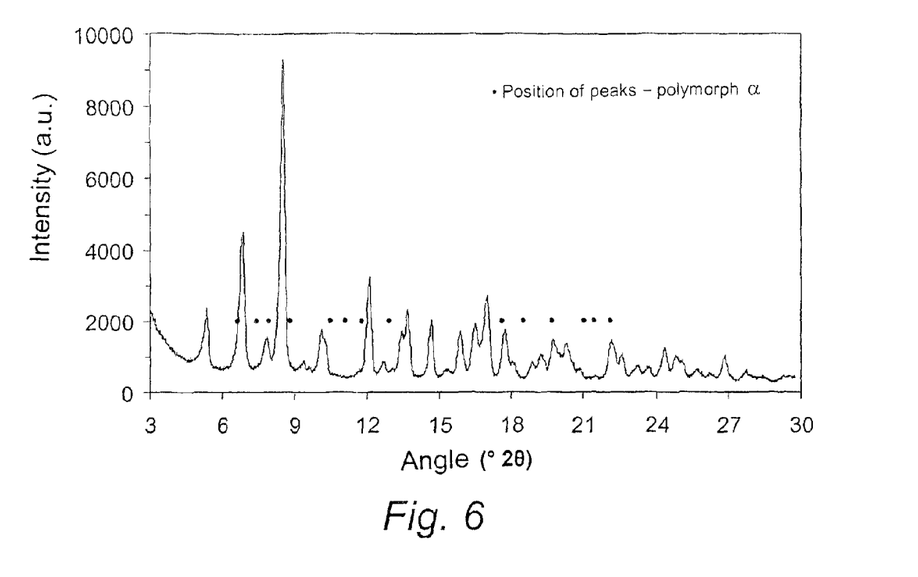
FIGS. 6 to 13 show, on the same diagram, a diffractogram of FIG. 1 and the positions of the characteristic peaks of the known polymorphs α, β, γ, δ, ε, ζ, ι and η, respectively.
Figure 7:
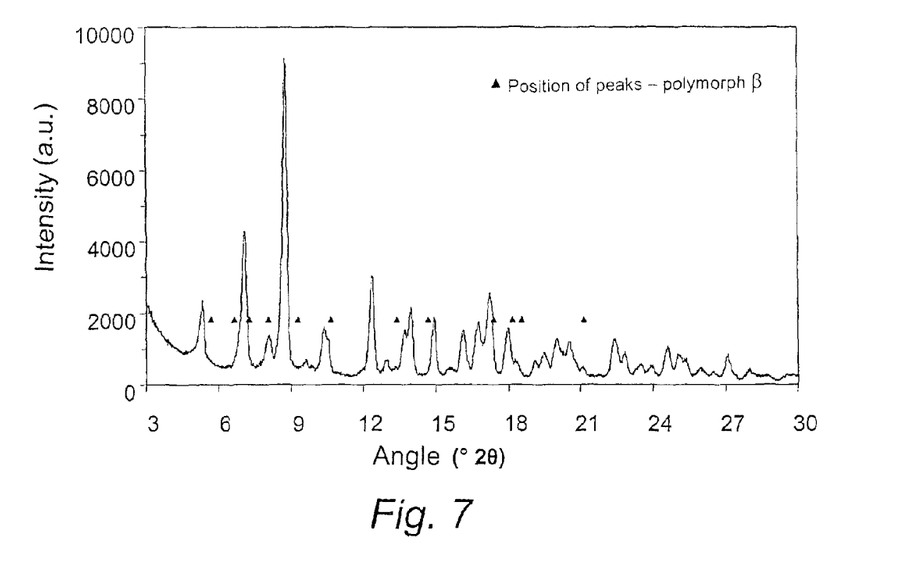
Figure 8:
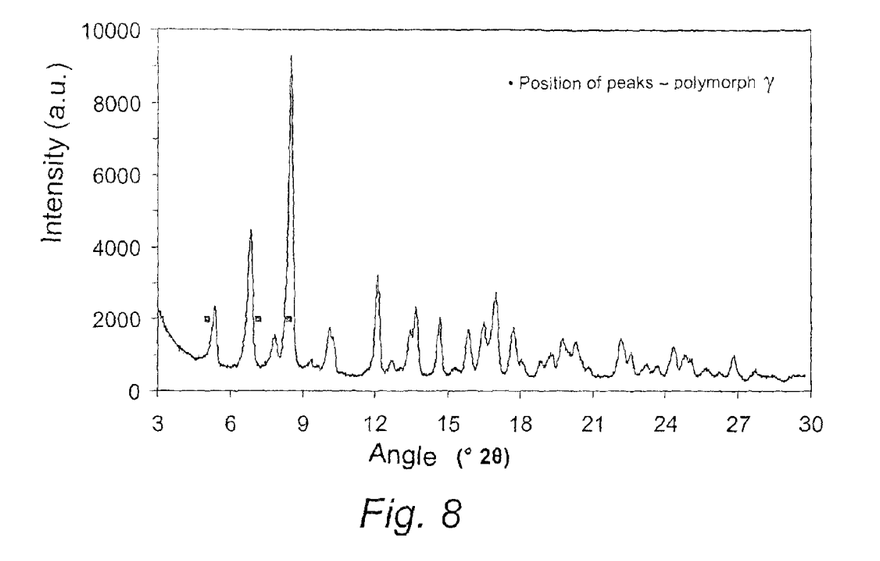
Figure 9:
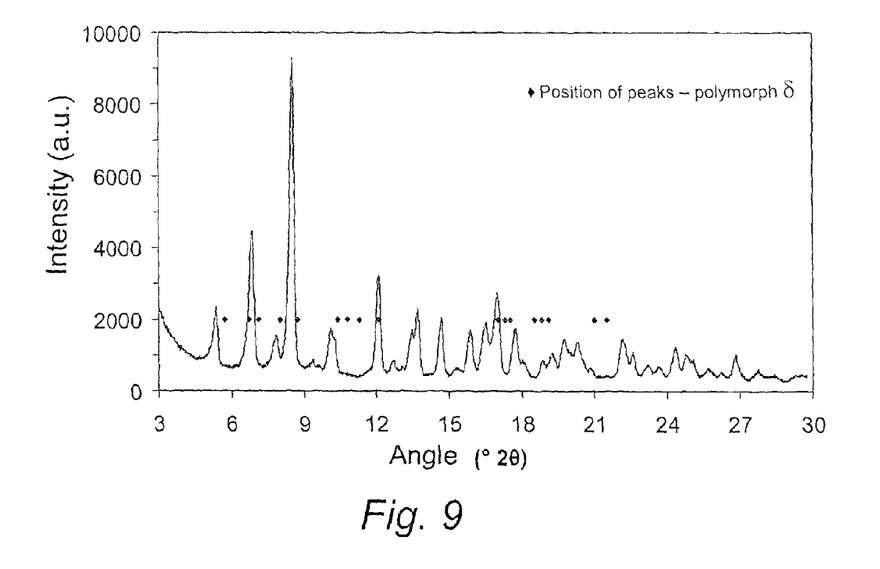
Figure 10:
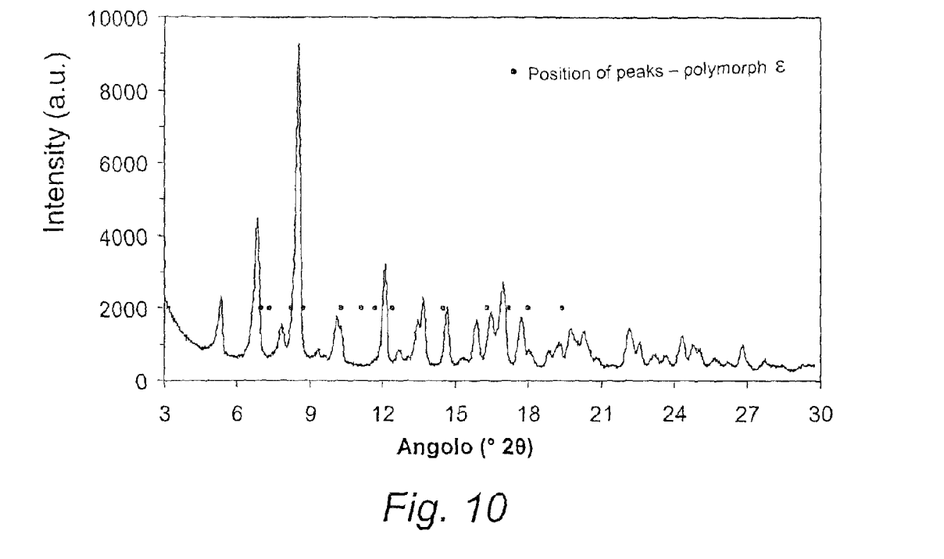
Figure 11:
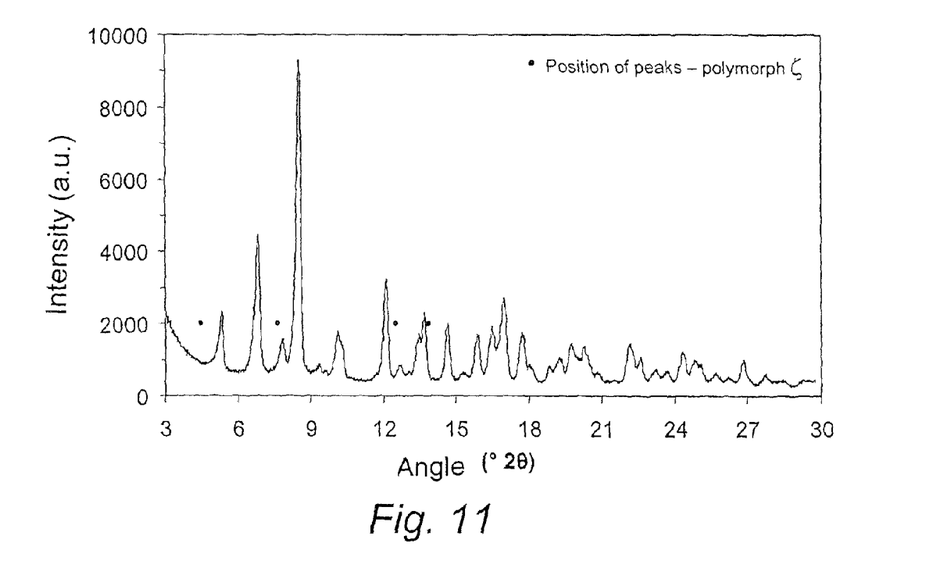
Figure 12:
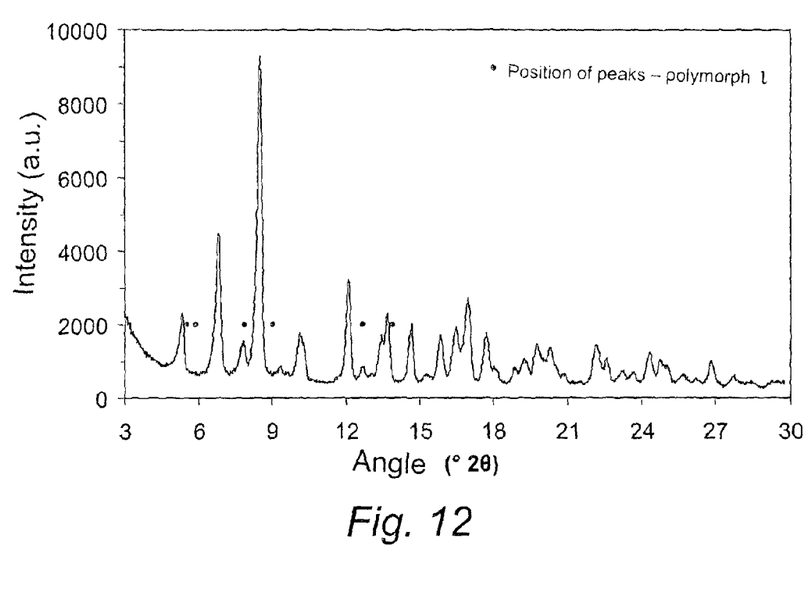
Figure 13:
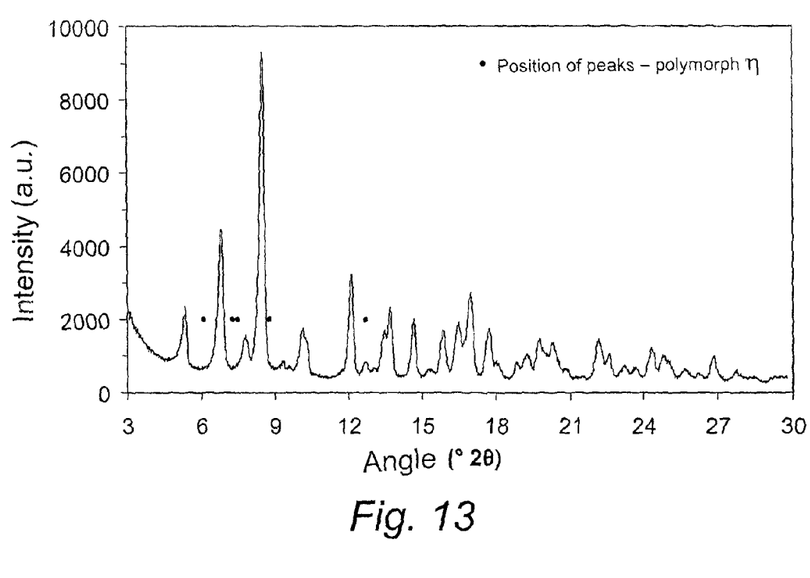

A powder XRD test was performed on the product thus obtained under the same conditions as in example 1, which resulted in the diffractogram shown as pattern e in FIG. 5.

EXAMPLE 7

The test of example 6 was repeated, but using a mixture of 10 ml of acetone and 30 ml of 1,2-dimethoxyethane as initial solvent.

11.20 g of pale orange wet product were obtained which, when dried in an oven under vacuum at 80° C. for 24 h, yielded 9.59 g of yellow-orange dry product.

A powder XRD test was performed on the product thus obtained under the same conditions as in example 1, which resulted in a diffractogram that was practically identical to that of the sample produced in example 5 (pattern not shown in the figures).

EXAMPLE 8

The test of example 6 was repeated, but using a mixture of 10 ml of ethyl acetate and 30 ml of 1,2-dimethoxyethane as initial solvent.

11.51 g of pale orange wet product were obtained which, when dried in an oven under vacuum at 80° C. for 24 h, yielded 9.60 g of yellow-orange dry product.

A powder XRD test was performed on the product thus obtained under the same conditions as in example 1, which resulted in a diffractogram that was practically identical to that of the sample produced in example 5 (pattern not shown in the figures).

EXAMPLE 9

The test of example 6 was repeated, but using a mixture of 5 ml of methanol and 30 ml of 1,2-dimethoxyethane as initial solvent.

In this case, it took approximately 6 hours to achieve spontaneous crystallisation in an orange solid. The suspension was then left to stir for one night. The solid was filtered and washed twice with 10 ml of 1,2-dimethoxyethane.

The wet product was dried in an oven under vacuum at 80° C. for 24 h, obtaining 7.53 g of yellow-orange dry product.

A powder XRD test was performed on the product thus obtained under the same conditions as in example 1, which resulted in the diffractogram shown as pattern f in FIG. 5.

EXAMPLE 10

The test of example 9 was repeated, but using a mixture of 2.5 ml of methanol and 30 ml of 1,2-dimethoxyethane as initial solvent.

Approximately one hour after the complete solubilisation of the Rifaximin, the spontaneous crystallisation of an orange solid was observed, and after a few minutes there was rapid precipitation. The suspension was left under agitation at room temperature throughout the night. The solid was filtered and washed twice with 10 ml of 1,2-dimethoxyethane.

The wet product was dried in an oven under vacuum at 80° C. for 24 h, obtaining 9.38 g of yellow-orange dry product.

A powder XRD test was performed on the product thus obtained under the same conditions as in example 1, which resulted in the diffractogram shown as pattern g in FIG. 5.

Further preparations were then carried out, varying the temperature of precipitation, as indicated in examples 11-13, the isolated powders have particle sizes with d (0.5) higher than 50 microns.

EXAMPLE 11

40.0 g of Rifaximin, 40 ml of absolute ethanol and 40 ml of 1,2-dimethoxyethane were charged into a 500-ml flask under nitrogen flow. The mixture was stirred and heated to reflux (74° C.). A perfectly clear, dark red solution was initially obtained. While always maintaining the reflux, the suspension was diluted with 160 ml of 1,2-dimethoxyethane, and spontaneously after about 30 minutes (78° C.) the formation of the first crystals was observed. After massive precipitation of the product, the suspension was cooled to 20° C., and the wet solid was filtered and washed with 2×25 ml of 1,2-dimethoxyethane.

38.66 g of wet product were obtained, which were dried in an oven under vacuum at 80° C. for 48 h.

The yield in "K form" Rifaximin as a large dry crystal was 32.0 g.

A set of tests was carried out, varying the starting ratio of absolute ethanol:1,2-dimethoxyethane from 10:90 to 50:50. The temperature of precipitation of the polymorph of the invention varied from 30° C. to the boiling point of the ethanol-1,2-dimethoxyethane mixture (approximately 80° C.).

The higher the precipitation temperature, the greater was the size of the crystal obtained.

The polymorph obtained in all cases presented a diffractogram that was identical to the diffractogram of FIG. 1.

EXAMPLE 12

20.0 g of Rifaximin and 40 ml of acetonitrile were charged into a 250-ml flask in a nitrogen atmosphere. Stirring was then started and the mixture was heated to reflux. (74° C.). To the dark red, clear solution 100 ml of 1,2-dimethoxyethane were added while maintaining the reflux. 40 ml of solvent were then distilled without applying vacuum. Cooling was then carried out slowly, and at 63° C. spontaneous crystallisation of the product began. The mixture was kept at 63° C. so as to achieve massive precipitation of the product.

The suspension was cooled to 20° C. The wet solid was filtered and washed with 2×10 ml of solvent.

18.68 g of wet product were obtained, which were dried in an oven under vacuum at 80° C. for 48 h.

The yield of Rifaximin κ as a large dry crystal was 16.73 g. The polymorph obtained showed a diffractogram identical to the diffractogram FIG. 1.

EXAMPLE 13

20.0 g of Rifaximin and 40 ml of acetone were charged into a 250-ml flask in a nitrogen atmosphere, stirring was started and the mixture was heated to reflux. (55° C.). To the dark red, clear solution 100 ml of 1,2-dimethoxyethane was added 30 while maintaining the reflux. The reflux temperature then increased to 700 C and at this point 50 ml of solvent were distilled without applying vacuum. Still under reflux, spontaneous crystallisation of the product began, and this temperature was maintained until there was massive precipitation of the product. The suspension was cooed to 20° C., the wet solid was filtered and washed with 2×10 ml of solvent.

21.00 g of wet product were obtained, which were dried in an oven under vacuum at 80° C. for 48 h.

The yield of Rifaximin κ as a large dry crystal was 18.77 g.

The polymorph obtained presented a diffractogram identical to the diffractogram in FIG. 1.

From the patterns shown in FIGS. 1 to 5 it is noted that, under all the conditions of preparation described in examples 1-13, the same crystalline form is always achieved, the polymorph κ of Rifaximin of the invention.

Conversely, FIGS. 6 to 13 present the pattern of FIG. 1, indicating the position of principal peaks of the known polymorphic forms α, β, γ, δ, ε, ζ, ι and η, showing that the pattern obtained with the polymorph of the invention does not correspond to that of any of the previously known polymorphs.

EXAMPLE 14

Stability testing of the polymorph of Rifaximin following conditioning in a humid atmosphere.

Two samples of the polymorphic form κ of Rifaximin: 63/11A, which was obtained by means of the procedure of example 4, and 69/11B, which was obtained by means of the procedure of example 1, were maintained for 24 hours in an environment of relative humidity equal to 80%. At the end of the conditioning, an increase of approximately 3%, ascribable to the adsorption of water from the environment, was recorded.

Figure 14:
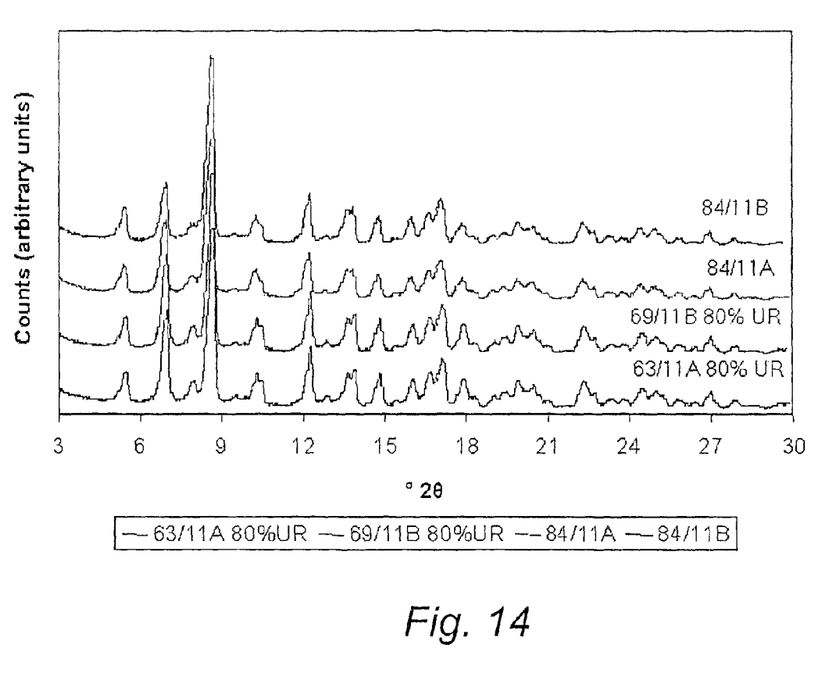
FIG. 14 presents the XRPD patterns of the polymorph of example 4, and of example 1 before and after conditioning with humidity values of 80%.

FIG. 14 shows the XRPD patterns samples pre/post-conditioning at humidity values of 80%, indicated as 63/11A 80% UR corresponding to the sample of example 4 post-conditioning at humidity of 80%, 69/11B 80% UR corresponding to the sample of example 1 post-conditioning at humidity of 80%, 84/11A and 84/11B, corresponding, respectively, to the samples of examples 4 and 1 before conditioning at 80% humidity.

These patterns were substantially identical to one another and overlapping with respect to the characteristic pattern of the polymorph κ of Rifaximin, confirming the excellent stability of the polymorph of the invention.

EXAMPLE 15

The polymorph obtained with the procedure described in example 2 was exposed at room temperature to variable relative humidity for a time period of 12 days, and then for a period of 5 months. When the humidity was increased, there were increases in the mass as shown in Table 2 for 12 days and Table 3 for 5 months.

TABLE 2

| % water following exposure to 80% and 45% humidity | | Total days |
|---|---|---|
| initial | 1.85 | 0 |
| RH 80% 4 days | 4.66 | 4 |
| RH 45% 3 days | 3.40 | 7 |
| RH 80% 4 days | 4.52 | 11 |
| RH 45% 1 day | 3.43 | 12 |

TABLE 3

| % water after exposure to 80% humidity (RH 80%) | |
|---|---|
| initial | 1.85 |
| 4 days | 4.38 |
| 7 days | 4.44 |
| 14 days | 4.37 |
| 1 month | 4.38 |
| 2 months | 4.45 |
| 5 months | 4.55 |

From the data reported in Table 2, it is evident that the process of water adsorption of the polymorph is superficial and reversible.

As shown in Table 3, the polymorph of the invention, exposed for prolonged times to an room relative humidity of 80%, showed a maximum adsorption of 4.5%.

Following conditioning at 5 months, the polymorph of the invention was subjected again to DRX analysis, and the pattern resulted to correspond to that one shown in FIG. 1, confirming the stability of the crystalline form κ of Rifaximin of the invention.

The invention claimed is:

1. A crystalline form κ of Rifaximin, characterized by a powder XRD spectrum with peaks at values of the angle 2θ of 5.3°, 6.8°, 7.8°, 8.5°, 9.3°, 10.1°, 10.3°, 12.1°, 12.7°, 13.4°, 13.7°, 14.6°, 15.3°, 15.8°, 16.4°, 16.9°, 17.7°, 18.0°, 18.8°, 19.2°, 19.7°, 20.3° and 22.1°.

2. The crystalline form κ of Rifaximin according to claim 1 having an XRD spectrum as shown in FIG. 1.

3. The crystalline form κ of Rifaximin according to claim 1 having an orthorhombic crystalline cell and belonging to the spatial group $P222_1$ with the following cell values:

| | |
|---|---|
| a (Å) | 24.07 ± 7 |
| b (Å) | 22.98 ± 5 |
| c (Å) | 15.34 ± 5 |
| α (deg) | 90.00 |
| β (deg) | 90.00 |
| γ (deg) | 90.00. |

4. The crystalline form κ of Rifaximin according to claim 3, having the following cell values:

| | |
|---|---|
| a (Å) | 24.0773 ± 12 |
| b (Å) | 22.9863 ± 12 |
| c (Å) | 15.3462 ± 10 |
| α (deg) | 90.00 |
| β (deg) | 90.00 |
| γ (deg) | 90.00 |
| Volume (Å3/cell) | 8493.30 ± 15. |

5. A process for obtaining the crystalline form κ of Rifaximin according to claim 1, characterized in that it includes the following steps:
   contacting the Rifaximin or non-dried Rifaximin with a 1,2-dimethoxyethane based solvent,
   recovering the obtained product in crystalline form, and
   drying in order to remove said 1,2-dimethoxyethane based solvent.

6. The process according to claim 5, comprising the following steps:
   suspending or dissolving Rifaximin or non-dried Rifaximin in 1,2-dimethoxyethane or in a solvent mixture containing 1,2-dimethoxyethane, in ratios such that the molar ratio 1,2-dimethoxyethane:Rifaximin is 1:1 or higher;
   filtering the obtained precipitate;
   drying the filtered product at a temperature of at least 60° C.

7. The process according to claim 5, wherein 1,2-dimethoxyethane is used as the only solvent in an amount equal to or greater than 3 ml per gram of Rifaximin.

8. The process according to claim 7, wherein the amount of 1,2-dimethoxyethane is lower than 10 ml per gram of Rifaximin.

9. The process according to claim 5, wherein 1,2-dimethoxyethane is used in mixture with one or more other solvents selected from n-heptane, methanol, acetonitrile, R—COO—$R^1$ esters, wherein R and $R^1$ are independently $C_3$-$C_6$ alkyl radicals, and $C_3$-$C_7$ alkyl ketones, ethanol, isopropanol and water.

10. The process according to claim 5 carried out in a protected atmosphere.

11. The process according to claim 10, wherein the protected atmosphere consists carrying out the process under nitrogen flow.

12. A pharmaceutical composition comprising a therapeutically effective amount of the crystalline form κ of Rifaximin according to claim 1 and a pharmaceutically acceptable carrier.

13. A method for the treatment of an individual suffering from a gastrointestinal tract condition, wherein the gastrointestinal tract condition is selected from diarrhea, hepatic encephalopathy, irritable bowel syndrome, Crohn's disease and diverticulitis said method comprising
   administering an effective amount of the crystalline form κ of Rifaximin according to claim 1 to said individual; and
   treating said individual.

14. The method according to claim 13, wherein said effective amount is from 20 to 2500 mg per day.

15. The method according to claim 13, wherein said effective amount is from 50 to 1000 mg/day.

16. The method according to claim 13, wherein said effective amount is from 100 to 600 mg/day.

17. A method for the treatment of an individual suffering from diarrhea or *E. coli*-derived pathologies with crystalline form κ of Rifaximin, said method comprising:
   administering an effective amount of the crystalline form κ of Rifaximin according to claim 1 to said individual and treating said individual.

18. The method according to claim 17, wherein said effective amount is from 20 to 2500 mg per day.

* * * * *